(12) United States Patent
Corey

(10) Patent No.: US 9,265,953 B2
(45) Date of Patent: *Feb. 23, 2016

(54) HANDLING RACE CONDITIONS DURING DATA TRANSFER BETWEEN MULTIPLE MODULES OF AN ELECTRONIC DEVICE

(75) Inventor: Robert A. Corey, Arden Hills, MN (US)

(73) Assignee: Medtronic, Inc., Minneapolis, MN (US)

( * ) Notice: Subject to any disclaimer, the term of this patent is extended or adjusted under 35 U.S.C. 154(b) by 948 days.

This patent is subject to a terminal disclaimer.

(21) Appl. No.: 13/455,264

(22) Filed: Apr. 25, 2012

(65) Prior Publication Data

US 2013/0289635 A1   Oct. 31, 2013

(51) Int. Cl.
| A61N 1/365 | (2006.01) |
| G06F 1/08 | (2006.01) |
| A61N 1/37 | (2006.01) |

(52) U.S. Cl.
CPC .............. *A61N 1/36507* (2013.01); *A61N 1/37* (2013.01); *G06F 1/08* (2013.01)

(58) Field of Classification Search
CPC ........................................................ G06F 1/08
USPC ........................................................ 713/500
See application file for complete search history.

(56) References Cited

U.S. PATENT DOCUMENTS

| 4,449,182 A | 5/1984 | Rubinson et al. |
| 4,890,224 A | 12/1989 | Fremont |
| 5,022,395 A | 6/1991 | Russie |
| 5,467,464 A | 11/1995 | Oprescu et al. |
| 5,758,131 A | 5/1998 | Taylor |
| 5,818,263 A | 10/1998 | Ashuri |
| 5,867,453 A | 2/1999 | Wang et al. |
| 5,987,081 A | 11/1999 | Csoppenszky et al. |
| 6,047,382 A | 4/2000 | Maley et al. |
| 6,324,426 B1 | 11/2001 | Thompson |
| 6,425,088 B1 * | 7/2002 | Yasukawa et al. ............ 713/400 |
| 6,667,645 B1 | 12/2003 | Fletcher et al. |
| 6,691,272 B2 | 2/2004 | Azim |
| 6,756,808 B2 | 6/2004 | Furuya |
| 6,907,538 B1 * | 6/2005 | Boutaud ....................... 713/400 |
| 7,027,542 B1 * | 4/2006 | Shihadeh ...................... 375/354 |
| 7,069,367 B2 | 6/2006 | Poisner et al. |

(Continued)

FOREIGN PATENT DOCUMENTS

WO   2010/070530 A1   6/2010

OTHER PUBLICATIONS

Office Action mailed on Jun. 5, 2014, for Related U.S. Appl. No. 13/455,256, 11 pages.

(Continued)

*Primary Examiner* — Suresh Suryawanshi
(74) *Attorney, Agent, or Firm* — Evans M. Mburu

(57) ABSTRACT

The accuracy of data processing operations in an electronic device is improved through reductions in errors associated with data acquisition, reading, and transmission. In one embodiment, two or more modules of an integrated circuit are operated at different clock speeds and a voting scheme is utilized to obtain a valid data value from one of the modules. The disclosure describes methods, devices and systems that utilize the voting schemes to eliminate errors induced by race conditions in obtaining valid data values during data transfer by obtaining a plurality of data samples while the communicating modules are operating at the different clock speeds and selecting from among the data samples the valid data value.

18 Claims, 7 Drawing Sheets

(56) References Cited

U.S. PATENT DOCUMENTS

| | | |
|---|---|---|
| 7,116,152 B2 | 10/2006 | Kwon |
| 7,245,446 B1 | 7/2007 | Lam |
| 7,617,409 B2 | 11/2009 | Gilday et al. |
| 7,962,805 B1 | 6/2011 | Priel et al. |
| 8,027,420 B2 | 9/2011 | McCabe |
| 8,060,204 B2 | 11/2011 | Huelskamp et al. |
| 8,185,812 B2 * | 5/2012 | Das et al. ............ 714/814 |
| 2002/0087146 A1 | 7/2002 | Schu et al. |
| 2002/0112058 A1 | 8/2002 | Weisman et al. |
| 2003/0056137 A1 | 3/2003 | Huelskamp |
| 2003/0151425 A1 | 8/2003 | Hagedorn |
| 2008/0086624 A1 | 4/2008 | Bull et al. |

OTHER PUBLICATIONS

Response filed on Sep. 5, 2014, for U.S. Appl. No. 13/455,256, 8 pages.

Notice of Allowance mailed on Sep. 19, 2014, for U.S. Appl. No. 13/455,256, 18 pages.

Corey, "Systems and Methods for Handling Race Conditions During Data Transfer in an Implantable Medical Device" U.S. Appl. No. 13/455,256, filed Apr. 25, 2012, 29 pages.

Corey, "Declaration under 37 C.F.R. 1.132," Signed Apr. 25, 2012, 3 pages.

* cited by examiner

HANDLING RACE CONDITIONS DURING DATA TRANSFER BETWEEN MULTIPLE MODULES OF AN ELECTRONIC DEVICE

FIELD

The disclosure relates generally to implantable medical devices of the type comprising integrated circuitry for performing monitoring of a physiologic state and/or therapy delivery. In particular, the disclosure pertains to improving the processing capabilities of such integrated circuits to improve accuracy of a data transfer impacted by race conditions.

CROSS REFERENCE TO RELATED APPLICATION

Reference is made to commonly-assigned application U.S. Ser. No. 13/455,256, now U.S. Pat. No. 8,942,337, filed concurrently, entitled "SYSTEMS AND METHODS FOR HANDLING RACE CONDITIONS DURING DATA TRANSFER IN AN IMPLANTABLE MEDICAL DEVICE" which is herein incorporated by reference in its entirety.

BACKGROUND

A wide variety of implantable medical devices (IMDs) that employ electronic circuitry for providing various therapies such as electrical stimulation of body tissue, monitoring a physiologic condition, and/or providing a substance are known in the art. For example, cardiac pacemakers and implantable cardioverter-defibrillators (ICDs) have been developed for maintaining a desired heart rate during episodes of bradycardia or for applying cardioversion or defibrillation therapies to the heart upon detection of serious arrhythmias. Other devices deliver drugs to the brain, muscle and organ tissues, and/or nerves for treatment of a variety of conditions.

Over the past 20 years, the IMDs have evolved from relatively bulky, crude, and short-lived devices to complex, long-lived, and miniaturized IMDs that are steadily being miniaturized with their functionality continuously increasing. For example, numerous improvements have been made in cardioversion/defibrillation leads and electrodes that have enabled the cardioversion/defibrillation energy to be precisely delivered about selected upper and lower heart chambers and thereby dramatically reducing the delivered shock energy required to cardiovert or defibrillate the heart chamber. Moreover, the high voltage output circuitry has been improved in many respects to provide monophasic, biphasic, or multi-phase cardioversion/defibrillation shock or pulse waveforms that are efficacious, sometimes with particular combinations of cardioversion/defibrillation electrodes, in lowering the required shock energy to cardiovert or defibrillate the heart.

The miniaturization of IMDs is driving size and cost reduction of all IMD components including the electronic circuitry components, where it is desirable to reduce the size so that the overall circuitry can be more compact. As the dimensions of the IMDs decreases, the electronic circuits of the IMD circuitry are preferred to decrease power consumption in order to maintain or increase longevity. Noticeably, the miniaturization of IMDs has taken advantage of the developments in CMOS (Complementary Metal-Oxide Semiconductor) technology, which has led to the development of single-chip processors (e.g., microprocessors) with ever increasing clocking speeds that can be clocked separately from other circuitry components of the IMD for efficient data processing and power management.

When there is a difference between the speed at which a signal input to a receiving circuit is transmitted and a speed at which the receiving circuit is enabled, a so-called race condition can occur. The race condition is manifested in many ways as has been discussed in the art. For example, depending on the relationship between the frequencies under which different circuits in an IMD are operated, the receiving circuit may attempt to sample the transmitted data during periods when the data is in a quasi-stable state. Such a state may exist during the active clock edge of the clock signals of the transmitting circuit. Attempts by the receiving circuit to read the data during such periods that are aligned with the active clock edges of the clock signal clocking the transmitting circuit may impact the integrity of data transferred between such circuits. As such, many solutions have focused on avoiding reading the data during such times as that where race conditions would arise to ensure that the data will be stable when sampled.

In conventional circuits, one such approach to transferring the data between circuits clocked at different speeds has been to skew the clocks. An example of this approach is discussed in U.S. Pat. No. 7,765,425 issued to Searles et al. In high frequency environments, the uncertainty in the timing relationship between the two clocks may approach the clock period of the faster clock signal and when this occurs, skewing the clocks is not sufficient to ensure accurate data transfer.

Another approach to eliminate the data and processing errors associated with the so-called race condition has been to turn off the higher frequency clock or to inhibit the higher frequency signal during the data transfer operations. By doing so, the circuits of the IMD are operated only under the lower frequency signal generated by the lower frequency clock during the data transfer operations. An example of such an approach is discussed in commonly assigned U.S. Pat. No. 7,085,952 issued to Huelskamp and which is incorporated herein by reference in its entirety. The '952 patent discusses considerations that may be needed as a result of the transitions between the lower and higher clock frequency signals. Another example is discussed in U.S. Pat. No. 5,022,395 issued to Russie.

In yet another approach, the solution to race conditions is to synchronize the edges of the higher frequency clock with the edges of the lower frequency clock. Such a solution utilizes a clock synchronizer that may utilize a phase-locked loop (PLL) circuit to synchronize the clock edges. An example of this approach is discussed in U.S. Pat. No. 7,436,917 to Adkisson et al.

However, the conventional solutions result in increased overall circuitry components to achieve the desired functionality and increase the complexity of the IMD. Additionally, the solutions have resulted in increased latency as well as increased current drain.

The potential for realizing a race condition becomes even more pronounced with attempts at achieving higher and higher clocking speeds. The race conditions can cause the wrong data value to be read when the data is sampled which can cause inaccurate operation (e.g., glitches or spurious transitions, etc.) of the individual logic circuits and, therefore, of the overall circuitry in the IMD. In fact, such race conditions can adversely affect attempts to miniaturize and increase speeds in IMD circuitry.

It is desirable to continue to reduce size and power consumption while increasing and improving processing capabilities of such IMDs.

SUMMARY

Generally, the present disclosure provides an improved method and system for communicating data between a first component and a second component of a device. The disclosure addresses race conditions that may affect the accuracy of data communication between the first component and the second component. This may arise, for example, when the first component is clocked by a clock signal having a first frequency and the second component is clocked by a second clock having a second clock frequency that is different from the first frequency.

In the present disclosure, a voting scheme is utilized by a data transfer module to read data to be transmitted from a second component that is clocked by the second clock signal for transfer to the first component. The data transfer module samples the data at the first clock signal speed. In some embodiments, the frequency of the first clock signal may be higher than the frequency of the second clock signal. The read operations, also known as data sampling, are performed on a defined active edge of the first clock signal. In one embodiment, the data sampling may be performed on the rising and falling edges of the first clock signal. In another embodiment, the data sampling is performed only on one of the rising or falling edge of the first clock signal.

According to the voting scheme, a plurality of samples of the data are obtained within a sampling window. The sampling window is defined based on the interval between the active clock edges of the second clock signal and a transition window of the second component. In one embodiment, the active clock edges of the second clock signal are the rising edges of the second clock signal. In that embodiment, the sampling window is less than the interval between two successive rising edges of the second clock signal. In another embodiment, both the rising and falling edges of the second clock signal are active. In that embodiment, the sampling window is defined to be less than the interval between successive rising and falling edges of the second clock signal.

In a further aspect of the voting scheme, the interval between each of the read operations is defined to be greater than the transition window for the transmitted data. In other words, the interval between a first read operation and a second read operation is defined to be greater than the transition window for data at the second component. In another embodiment, a method for communicating data that is transmitted to a first component by a second component is disclosed. The first component may be clocked at a frequency that is higher than the clocking frequency of the second component. In accordance with the method, a plurality of samples of the data are obtained by the first component within a sampling window.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

The present disclosure can be practiced in the context of the systems described herein. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discrete processes involving collecting, storing, and presenting physiologic trends of a patient, as well as in delivering therapies (e.g., a cardiac therapy). The battery located within an implantable medical device (IMD) provides the power necessary for performing such operations. Therefore, conserving battery power can provide for longer, uninterrupted operation of the IMD. Many techniques have been utilized in order to conserve power. One such approach utilizes two or more clock rates for multiple circuits within the IMD. For example, a first (e.g., faster) frequency clock is invoked in order to process acquired physiologic data with complex circuitry in the IMD and deliver a cardiac therapy in response to the processing of the physiologic data. Meanwhile, the monitoring functions for acquisition of the physiologic data may be performed under operation of a second (e.g., slower) clock frequency.

However, certain errors, ringing, false signal rises (glitches), etc., may occur when communicating among the differently clocked circuits, or when transferring data from one circuit to another that can cause inaccuracies in the data and compromise the integrity of the operation of the circuitry making the IMD operation unreliable. The various circuits or component of the IMD that are clocked by the first clock must nevertheless communicate with other components of the IMD that are operated under control of the second clock such that data is conveyed between the first component and the second component.

Figure 1:
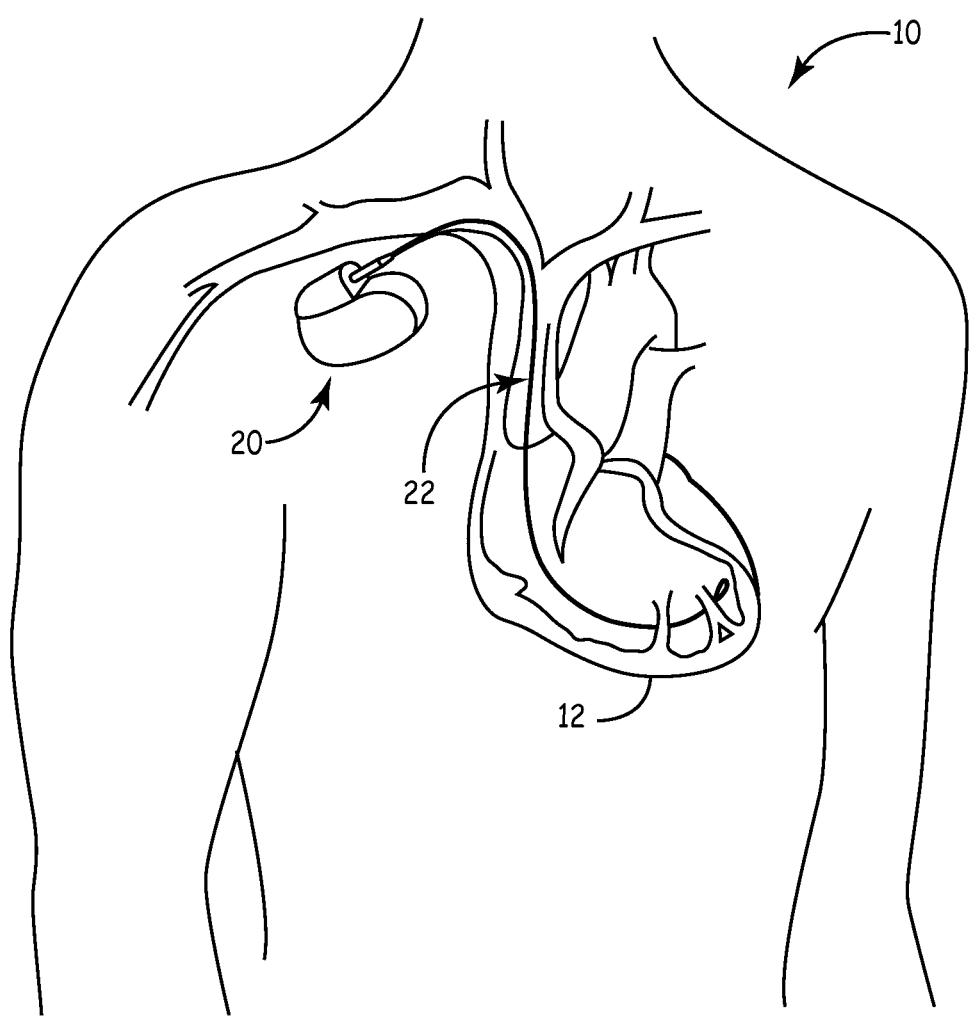
FIG. 1 illustrates an implantable system in accordance with one exemplary embodiment of the disclosure.

FIG. 1 illustrates an implantable system in accordance with one exemplary embodiment of the disclosure. An implantable medical device (IMD) 20 is implanted in a body 10 near a heart 12. IMD 20 includes circuitry, a battery and other components that are contained within a hermetically sealed, biologically inert outer canister or housing that may be conductive so as to serve as a pace/sense electrode in the pacing/sensing circuit. One or more leads, collectively identified with reference numeral 22, electrically couple to the IMD 20 and extend into the heart 12. In the case where device 20 is a pacemaker, leads 22 are pacing and sensing leads to sense electrical signals attendant to the depolarization and repolarization of the heart 12 and provide pacing pulses in the vicinity of the distal ends thereof. One or more exposed conductive pace/sense electrode(s) for sensing electrical cardiac signals or delivering electrical pacing pulses to the heart 12 are disposed at or near the distal ends of the leads 22. The leads 22 may be implanted with their distal ends situated in the atrium and/or ventricles of the heart 12 or elsewhere in cardiac blood vessels in operative relation with a heart chamber. The leads 22 can also carry other sensors for sensing cardiac physiologic data, e.g. pressure, temperature, impedance, pH, blood gas, acceleration, etc.

IMD 20 may also be a pacemaker/cardioverter/defibrillator (PCD) corresponding to any of the various commercially-available implantable PCDs. Those and other alternative implantable devices may be employed using the present disclosure in that such devices may employ or be modified with circuitry and/or systems according to the present disclosure. Examples of such alternative devices of IMD 20 may be an implantable nerve stimulator or muscle stimulator. In fact, the present disclosure is believed to find wide application in any form of electrical device which uses CMOS, CML, SOS, SOI, BICMOS, PMOS, and/or NMOS devices, and is further believed to be particularly advantageous where low power consumption is desired, particularly in battery powered devices.

In general, IMD 20 includes a hermetically-sealed enclosure that includes a power source and circuitry to control therapy delivery to heart 12. The circuitry may be implemented in discrete logic and/or may include a microcomputer-based system with A/D conversion.

Figure 2:
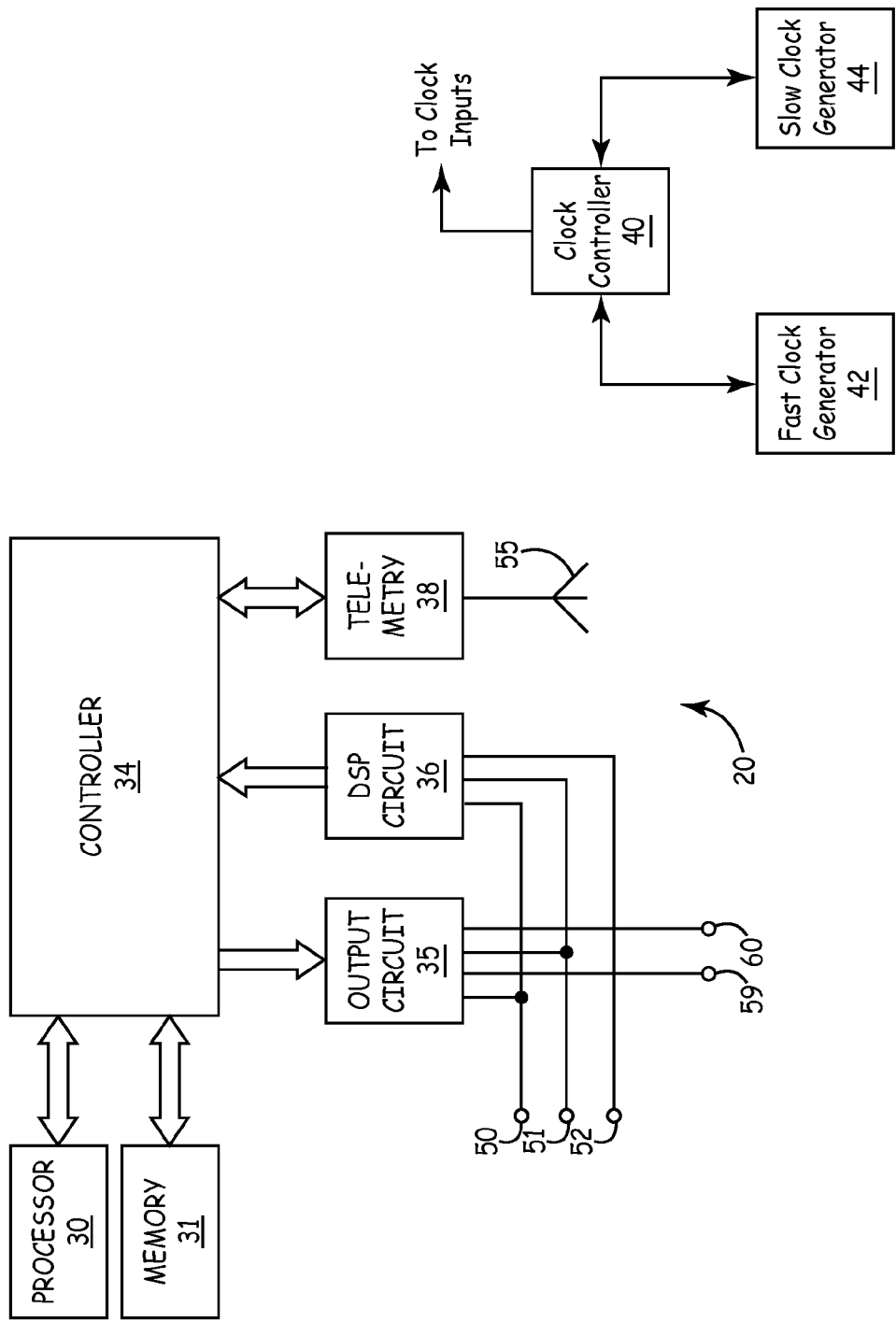
FIG. 2 illustrates a simplified functional block diagram of an implantable medical device.

Referring now to FIG. 2, a simplified functional block diagram of IMD 20 is illustrated. The IMD 20 is an example of the type of devices in which the present disclosure can be implemented. Accordingly, FIG. 2 is considered to be exemplary rather than limiting with regard to the present disclosure. It should be noted that the discussed aspects of the IMD 20 could be implemented as a wide variety of devices, including pacemakers, defibrillators, etc. Further, the IMD 20 can be applied to single chamber, dual chamber and multi-chamber systems.

The components of the IMD 20 illustrated in FIG. 2 are microprocessor 30, memory 31, a digital controller 34, output circuit 35, a digital signal processing (DSP) circuit 36, a telemetry/programming unit 38, a clock controller 40, a first (faster) frequency clock generator 42, and a second (slower) frequency clock generator 44. The designations "faster" and "slower" are provided to indicate the relative speeds of the clock generators in one embodiment. In other embodiments, the relative speeds may be reversed, while in other embodiments, additional (e.g., fourth, fifth, seventh and so forth) clock generators may be provided for differing additional frequency speeds. Although not illustrated in the figures, various components of the IMD 20 are communicatively coupled to each other for transfer of data between the components.

Examples of coupling techniques for communication between the components include a communication bus or a conductive pathway and the data that is transferred from one circuit or component to another circuit is propagated through such coupling medium. In accordance with aspects of the present disclosure, various standard communication interfaces such as the serial peripheral interface (SPI) or the inter-integrated circuit ($I^2C$) may be utilized for communication between the components of the IMD 20.

There are a number of reasons for having multiple clocks clocking separate circuits or components in the IMD 20. For one, it may be desirable for different circuits to be enabled at different times. That is, it may be desirable to turn clocks on and off in order to save power, i.e., using clocks only when they are actually doing work and not just running all the time. Another design consideration may be the need to provide local clock signals in different circuits in view of the characteristics associated with each of the different circuits. In an example embodiment, a slower clock signal of 5 kilohertz (KHz) is generated to clock the digital controller 34, the output circuit 35, the DSP circuit 36, the telemetry/programming unit 38 and the clock controller 40. The 5 KHz clock signals may be generated by the second (slower) frequency clock generator 44. Each of these components may be implemented in digital circuitry or digital signal processors or the like, referred to herein as "hardware," and operated following defined state and state transitions of one or more finite state machine. Memory 31 may also be clocked by the slower frequency signals in some embodiments.

Memory 31 can include read only memory, typically used to store the basic programming for the IMD 20, including the primary instructions set defining the computations performed to derive the various timing intervals performed by IMD 20. Memory 31 can also include random access memory, typically used to store the values of variable control parameters, such as programmed pacing rate, pulse widths, pulse amplitudes, and so forth, which are programmed into IMD 20 by the physician.

The microprocessor 30 functions at a faster clock speed (i.e., generated by the first frequency clock generator 42) under the control of software algorithms stored in memory unit 31 and in response to interrupts and handshake signals from the hardware to run various operations and to trigger operations of one or more of the hardware components of the IMD 20. For example, the microprocessor 30 operates the hardware to perform a plurality of operations, including memory access and storage operations, physiologic data processing, and therapy delivery operations. The microprocessor 30 communicates with the hardware components via an address and data bus (not shown) that can be implemented in an 8-bit or 16-bit parallel bus architecture. Data bits are transmitted over the coupling medium between the components of the IMD 20 and this transmission may be at a different clock speed. For example, transmission via the SPI may be at a frequency of 1.4 megahertz (MHz). The first (faster) frequency clock generator 42 generates a clock signal of a faster frequency in relation to the frequency generated by the second (slower) frequency clock generator 44. For example, the faster frequency may be approximately 2.8 MHZ and is provided in its raw form or divided down to meet the appropriate clocking speed for the high speed components such as the microprocessor 30. In one example, the microprocessor 30 is operated at a frequency of 700 KHz.

Controller 34 performs the basic timing and control functions of the IMD 20. Controller 34 would typically include at least one programmable timing counter, e.g., initiated on paced or sensed ventricular contractions, for timing out intervals thereafter. This timing counter is used to define the escape intervals for timing generation of pace pulses, as well as for timing the respective durations of the charge and recharge pulse portions of triphasic pulses. Controller 34 triggers output pulses to be generated and delivered from output stage 35, and it generates interrupts when the need arises to communicate with microprocessor 30 that is clocked at the faster clock speed. Among other things, a slower frequency clock may be employed to time out the intervals associated with therapy delivery and detection of sensed events in accordance with a programmed pacing mode and pacing parameters and/or cardioversion/defibrillation functions and the like, depending upon the particular IMD. The second (slower) frequency clock generator 44 provides the operational clock operable to control the functions of the pertinent circuitry of IMD 20.

The output circuit 35 is coupled to electrodes 50 and 51 which are employed both for delivery of pulses and for sensing of cardiac signals. Electrode 50 is typically located on the distal tip end of a lead and is preferably placed in the apex of the right ventricle for ventricular pacing; for atrial pacing, it is placed in the patient's atrium. Electrode 51 is typically a ring electrode, as used with a bipolar lead. Electrode 52 represents the device housing, which may be used as the indifferent electrode for selected unipolar pacing and/or sensing operations. For a dual or multi-chamber pacing system, additional electrodes are employed. For example, electrodes 59 and 60 may be used for pacing and sensing in the atrium, while electrodes 50 and 51 are used in the ventricle. Output circuit 35 is controlled by controller 34 to determine the amplitude and pulse width of the pulse to be delivered and to determine which electrode pair is to be employed to deliver the pulse. It should be noted that in some cases the electrodes 51 and 52 would be co-located on the device itself instead of being attached using leads.

Cardiac signals are sensed at a desired pair or pairs of electrodes. For example, bipolar and/or unipolar sensing may be used. In one embodiment, a unipolar lead in the atrium and a unipolar lead in the ventricle are used, e.g., the signals are picked up at electrodes 50 and 59. Sense signals are input into DSP circuit 36, which comprises a number of signal processing channels corresponding to signals of interest. For example, in a dual chamber pacemaker which incorporates P wave processing either for rate control, capture detection or any other reason, there would preferably be three channels for respective signal processing of the P, R and T waves. The data resulting from the digital signal processing performed by DSP circuit 36 is transmitted via a coupling medium, such as the SPI to processor 30, for the signal classification operations, as well as any other necessary calculations. External control of the implanted device is accomplished via telemetry/control block 38, which allows communication between the implanted device and an external programmer (not shown) via antenna 55.

Figure 3:
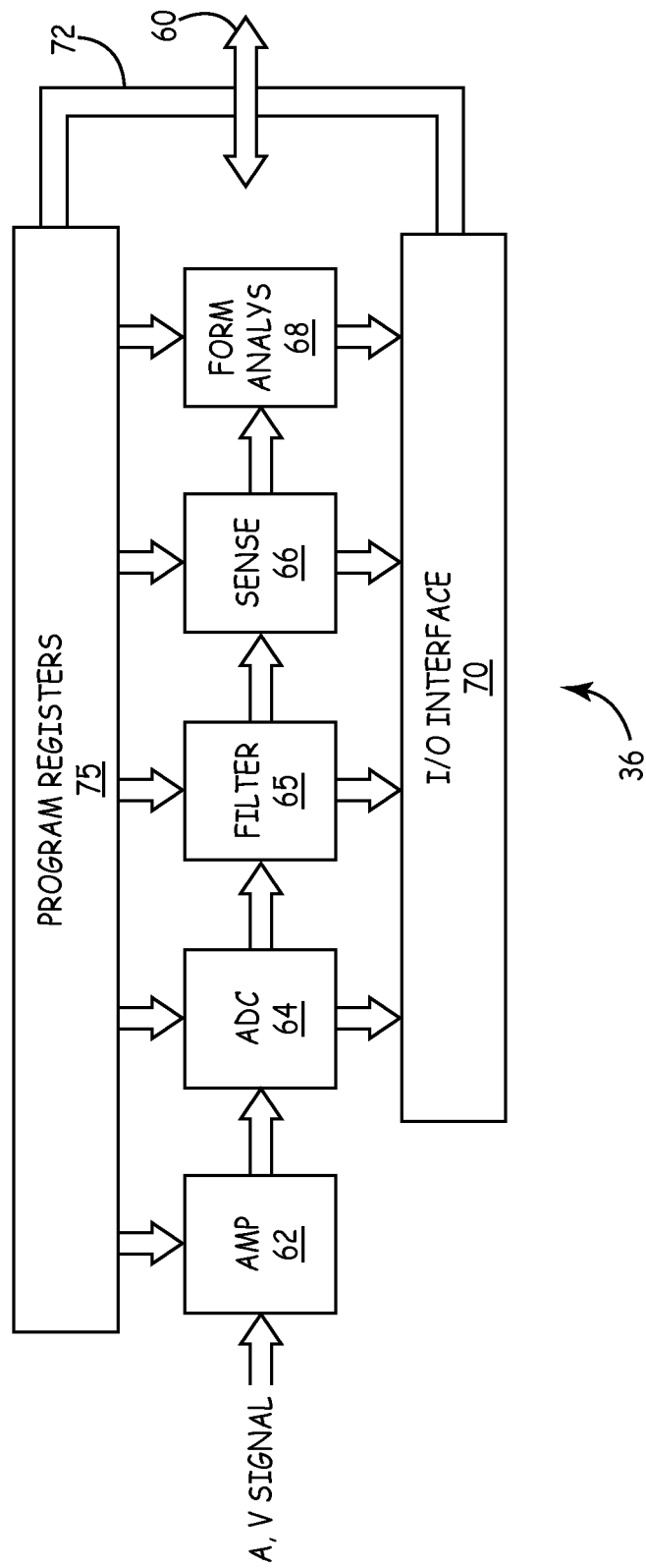
FIG. 3 depicts a block diagram representing the primary components of an exemplary circuit of FIG. 2.

FIG. 3 depicts a block diagram representing the primary components of the exemplary DSP circuit 36. The DSP circuit 36 is exemplary of the type of DSP devices that can be used to implement the present disclosure. The DSP circuit 36 illustrates a typical DSP channel that can be used to process received signals. It should be noted that this is a simplified example, and that typical DSP devices would suitably include a plurality of DSP channels used for signal processing of respective signals.

The DSP circuit 36 receives a waveform signal, typically an atrial (A) or ventricular (V) signal and processes the signal. The received signal may initially be processed through an amplifier 62. The amplified analog signal is passed into A/D converter 64, for sampling and generation of a corresponding digital signal. The A/D conversion is done by any suitable technique, such as with a delta-sigma modulator. The resulting digital signal from ADC 64 is passed to filter 65 which is suitably a digital bandpass filter having a characteristic to eliminate low frequency signal components and the offset of the converter, as well as to take out high frequency artifacts. The output of filter 65 is connected to sense block 66. Sense block 66 processes the filtered digital signal (referred to herein as SIG) to obtain the slew rate, or slope of the signal, also hereafter referred to as the SL signal, and then compares both the SIG and SL signals to plus and minus threshold voltages to derive a "sense" signal.

The "sense" signal is passed to the form analysis block 68. This block is where the DSP circuitry operates to extract parameters from the signal under examination. The parameters extracted from the waveform would typically depend on the specifics of the DSP implementation. As one example, the DSP implementation can extract nine morphological parameters, including the minimum amplitude and maximum amplitude of both the filtered cardiac signal and the slope of the filtered cardiac signal, the time from the start of the analysis window to those four amplitudes, and the signal width from the first threshold crossing to the last threshold crossing.

Within the circuitry of the IMD 20, data is often shared between the various circuitry of the IMD 20. For example, in accordance with the present disclosure, the results of the processing by DSP 36 may be communicated to other circuitry of the IMD 20 to control therapy delivery and other IMD functions. As explained above, the various circuitry may be connected to each other through a data bus such, for example, as the SPI bus.

Generally speaking, retrieval from, and transfer of data between, the various circuitry of the IMD 20 is prone to errors induced by race conditions. The race conditions referred to herein occur as a result of inaccuracies in the sampling (read) operations of data communicated between modules. These inaccuracies are in part due to the clocks that control operation of the modules being asynchronous and in part because of differing clock speeds. The conventional solution addressing the race conditions that is premised on utilizing a single frequency signal for the entire IMD has proven unacceptable. To illustrate, the faster frequency signal required to ensure timely operation by the microcontroller is too high for many of the circuits in the IMD and therefore would result in an excessive power drain and waste of the rather limited IMD battery resources. On the other end of the spectrum, the slower frequency signal utilized to power the various other circuits of the IMD is too low and incapable of running the microprocessor efficiently and therefore would limit the overall processing capability particularly in the implementation of complex computation algorithms.

Other conventional solutions that address the race conditions typically build in latency into the system or require some form of synchronization such that the relative timing of the clock edges of the clock signals clocking the communicating components can be discerned. Many of these conventional solutions also suffer from excessive current drain. In particular, the very act of sending a clock signal between components in a low power device such as many implantable medical devices will consume more current than the entire current budget of the chip for performing an operation. As such, two or more clocks are utilized to generate frequency signals having varying speeds to optimize operation of each module of the IMD.

Figure 4:
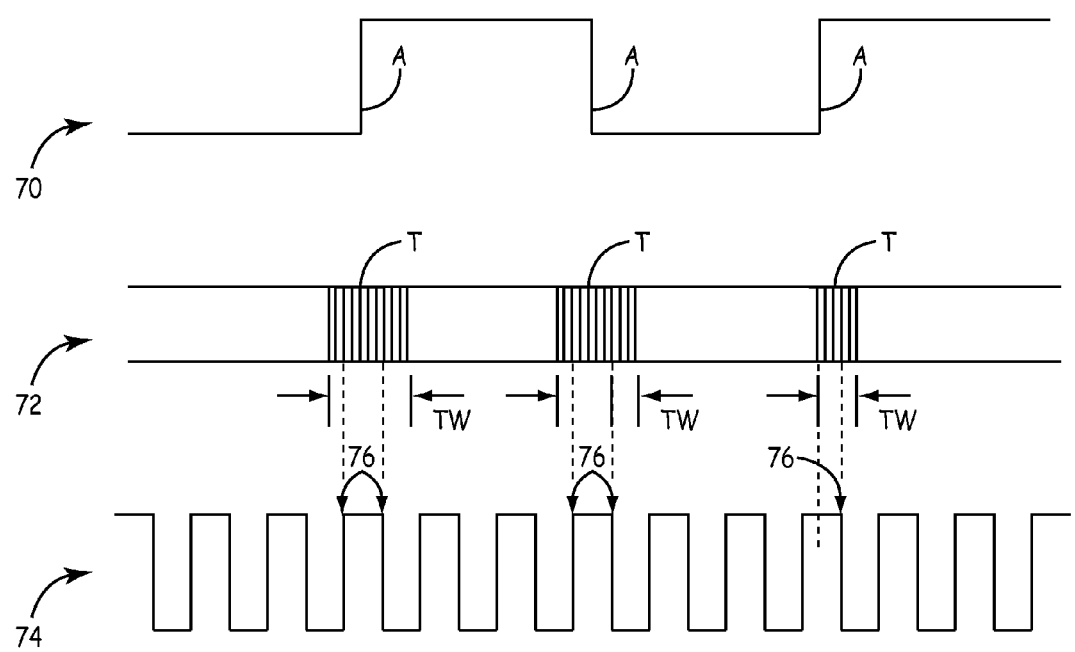
FIG. 4 illustrates an example of one type of race condition in accordance with the disclosure.

To provide additional context for the present disclosure, FIG. 4 illustrates an example of one type of race condition that is referred to herein and addressed by this disclosure. That race condition arises due to data transitions and like many other types of race conditions for which this disclosure is believed to have applicability, it affects the accuracy of data sampling. Generally, the data transitions occur at or around the active edges of the clock signal that is clocking a given chip. The active edges may be either or both the rising and falling edges of the clock signal. During any of these data transitions the data value may not exist in a stable state and therefore the data value cannot be guaranteed to be correct.

Turning to FIG. 4, the illustration depicts a clock signal 70 having a second (slower) clock speed. Below clock signal 70 is a data signal 72. This data signal 72 represents data that is communicated from a second component that is clocked by the second clock signal 70. The data may be generated within the second component or obtained from an external source, such as an electrode that measures physiologic signals representative of cardiac events, for transmission from the second component. The data on the data signal 72 will transition ("T") during an active edge of the clock signal 70. In the illustration, it is assumed that both the rising and falling edges of the clock signal are active edges, ("A"). As can be seen in FIG. 4, data on the data signal 72 will begin transitioning just after the rising edge and settle after a transition window ("TW") following the active edge. As used herein, the transition window refers to the window of time that data is unstable following an active clock edge. The transition window will generally vary depending on the design of the elements within the second component. For instance, in one embodiment, the component utilizes memory elements, such as flip flops, that are edge triggered for propagation of data. The transition window (TW) is therefore dependent on the technology of the flip flop element.

The next signal represents a clock signal 74 having a first (faster) clock speed. In the embodiment, the frequency of clock signal 74 is faster than that of the second clock signal. A first component that is clocked by the clock signal 74 may be communicatively coupled to the second component clocked by the clock signal 70. This first component may issue a read request for data in the second component and that data would be sampled at the active edges of the first clock signal 74 in accordance with an embodiment of this disclosure. Here, the active edge of clock signal 74 is defined to include both the rising edge and the falling edge. Because of the asynchronous relationship between clock signal 70 and clock signal 74, FIG. 4 shows that overlaps 76 may occur between the data transitions (T) around the active edges of clock signal 70 and the active edges of clock signal 74. In other words, because the first (faster) clock signal clocking the first component is not synchronized with the second (slower) clock signal clocking the second component, then the data to be read by the first component may transition concurrently with a sampling of the data during the active edge of the first (faster) clock signal. Consequently, attempts by the first component to sample the data on data signal 72 during periods of the transition T will result in sampling of an erroneous value. The condition in which the data is sampled as it is in the midst of transitioning is one example of a race condition.

The inventor has recognized the need for continued operation of the communicating components while minimizing current drain. The inventor has recognized that it may be desirable to maintain the operation of the components that are clocked by signals from both the first (faster) clock and the second (slower) clock during the data transfer operations. It is further desirable for such communication between the components to occur while minimizing current drain.

Accordingly, the present disclosure provides an alternative communication technique that enables continued operation of first circuitry clocked by the first (faster) frequency clock and the second circuitry clocked by the (slower) frequency clock while simultaneously performing data transfer operations between the first and second circuitry. Unlike conventional solutions that address the occurrence of race conditions by turning off one clock, or by synchronizing the clocks, or by the utilizing a buffer, the present disclosure addresses race conditions by utilizing a voting scheme.

The voting scheme may be implemented in a data transfer module that may reside on the transmitting (second) circuit or on the receiving (first) circuit or any other circuit of IMD 20. The data transfer module may comprise hardware or software, or firmware, or a combination of all three.

In one embodiment, the voting scheme may be implemented for communication between a first component that is clocked by a first clock signal and a second component that is clocked by a second clock signal different from the first clock signal. For example, the first clock signal may be faster than the second clock signal and the voting scheme would reside in the second component. In general, the voting scheme utilizes a set of conditions that guarantee the accuracy of data sampled by the receiving component.

In accordance with the present disclosure, data transfer in response to a read request by a first component, utilizing the voting scheme includes obtaining a plurality of samples of the data that is communicated from the second component. The plurality of samples may be obtained within a predefined duration that will be referred to herein as the sampling window. The sampling window, corresponding to the window of time within which multiple data samples are taken, is based on the individual transitions of the data at the transmitting component. In this instance, the transmitting component is the second component that is clocked by the second (slower) clock signal. Therefore, another way to describe the sampling window is that it is the time between the active edges of the second (slower) clock signal minus the transition window.

Further, the interval between each one of the plurality of samples obtained under the voting scheme within a given sampling window is defined to be greater than the transition window (TW). The interval between two consecutive individual samples is referred to herein as the sampling period. In other words, the sampling period is defined to be greater than the transition window (TW) of the data in the data signal that is being sampled by the first component. Defining the sampling period as such ensures that two consecutive samples cannot be obtained while the data at the sending component is in transition. However, the sampling period within a given sampling window or for multiple sampling windows can differ provided the requirement that each sampling period is greater than the transition window is met.

Figure 5:
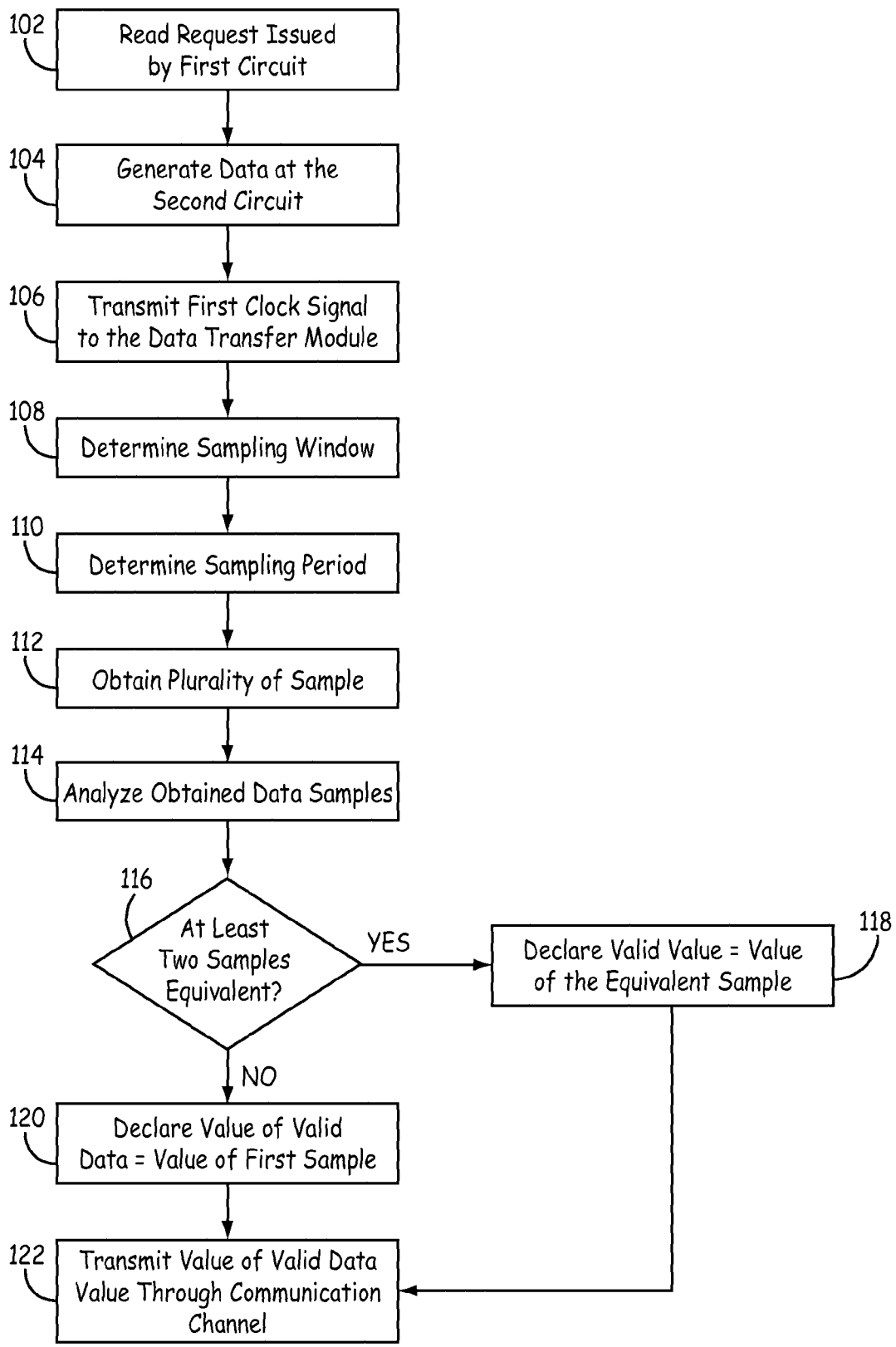
FIG. 5 illustrates a flow chart of a method for transferring data from one circuit to another in accordance with one embodiment of the disclosure.

Turning next to FIG. 5, a flow chart is described that illustrates one embodiment of the disclosure. Generally speaking, the embodiment discussed in FIG. 5 provides a solution to address race conditions that occur during transfers of data between a first component operating at a first clock speed and a second circuit operating at a second clock speed that is different from the first clock speed. The method may be initiated by a read request that is issued by a first component, for example the microprocessor 30 (102). The data to be transmitted may be generated either before or after the request for data is issued by the receiving component (104).

If the first (receiving) and second (transmitting) components are clocked at the same frequency and locked together in an appropriate phase relationship, no race condition would occur. However, constantly transmitting even moderate frequency clock signals between the components results in current drain that often exceeds the current drain of an entire component. This is a direct result of the large capacitances between components compared to within components.

It remains preferable to clock each of the first and second components with their respective clock signals. This leaves the first component vulnerable to sampling the data signal from the second component at a point during the active rising (positive) edge or active falling (negative) edge, of the second clock signal which results in a sampling of an indeterminate data value that is incorrect. For example, assuming a data sample having binary value 0000_0111, the value of the sample may transition to 0000_1000, i.e., increment by "1" during an active clock edge. If the data is sampled as it is transitioning at the second circuit, the data transfer module may sample one of 0000_0111, or 0000_1000, or 0000_1111, which are the values that the data is expected to transition between. Thus there is a likelihood that an incorrect data value will be sampled. To avoid this, the voting scheme of the present disclosure determines a valid data value during a data transfer operation between a circuit operating at a lower frequency clock and a circuit operating at a higher clock frequency.

Therefore, circuitry operating at the higher clock frequency, such as the microprocessor, can continue its processing operations even as it is reading data from other circuitry that is clocked at the lower frequency such as the hardware, which also proceeds with its operations during the data transfer.

In general, the data at the second circuit becomes valid after the transition window and remains valid until the next active edge of the clock signal. The data will transition during the transition window and during this time period, the data value is indeterminate. Reading the data value during the interval defined by this transitional time period may result in an erroneous reading.

Recognizing, as the inventor has, that the data transitions only occur at the active edge of the clock signal controlling the transmitting circuit, the erroneous readings can be mitigated by obtaining a plurality of samples in the period within two active edges of the controlling clock and at least one of those data samples will be valid. In one embodiment, to ensure the accuracy of data that is read by circuitry operating at a first clock speed from circuitry that is operating at a second clock speed, which is different from the first clock speed, the voting scheme as described in the present disclosure obtains a plurality of data samples within one period of the second clock speed.

With that in mind, one embodiment of the present disclosure entails obtaining three samples of data. In an implementation where the data transfer module resides in the second (transmitting) circuit, the first clock signal may be transmitted to the data transfer module for operation of the voting scheme (106). This step is optional depending upon the circuit in which the data transfer module resides.

An interval within which the plurality (e.g., three) of samples are obtained is determined (108). That interval is the sampling window. To establish the sampling window, the frequency of the second (slower) clock signal may obtained by the data transfer module. Alternatively, the frequencies of the transmitting and receiving circuits may be preprogrammed perhaps during initial circuit manufacture, or the speeds may be derived from measurements that are performed while the IMD 20 is operational. The sampling window is set to be less than the duration between two successive data transitions. Because the data will transition on the active edges of the second clock, the sampling window or the time within which the plurality (e.g., three) of samples is obtained is therefore based on the interval between successive active edges of the clock signal of the transmitting component. In this example, that clock signal is the second (slower) clock signal.

In accordance with the voting scheme, the sampling period—or interval between the sampling of each individual data value—for the plurality of data samples obtained within one sampling window is subsequently established (110). The sampling period is selected to be greater than the transition window for the data so as to prevent obtaining two samples while the data is unstable because of a transition. For example, in an edge triggered flip-flop, the data transitions will only occur at the active edge of the second clock with a settling time that is based on the technology of the flip flop manufacturer. Therefore, in the implementation of the voting scheme utilizing three samples, the sampling period is selected to be greater than the transition window to ensure that two consecutive samples will not both be obtained while the data is in transition.

The data transfer module will subsequently obtain the plurality of samples within the sampling window at intervals based on the sampling period (112). The data transfer module will obtain each of the samples at an active edge of the first clock signal. For example, the active edge may be the falling edge, or the rising edge, or both the falling and rising edges. Irrespective of the implementation, the plurality of samples will nevertheless be obtained within the defined sampling window, each being spaced apart by the sampling period.

With continued reference to FIG. 5, an evaluation is performed to determine a valid data value based on the plurality of data samples. The voting scheme performs a comparative assessment of the plurality of data samples and utilizes predetermined criteria to select the valid data value (114). In an embodiment, the voting scheme may compare all of the data samples to each other. In another embodiment, the voting scheme may compare only a subset of the data samples.

In accordance with one embodiment of the disclosure utilizing three consecutive samples, the analysis for aiding in the selection of the valid data value will be as follows. The three consecutive sample values are compared to each other to determine whether they are equivalent (116). In the comparison it is determined whether at least two of the three sample values are equivalent and if so, the valid data value is deemed equal to the value of the at least two equivalent sample values (118). The two equivalent sample values may be those that are immediately consecutive to one another or the first and third of the three sample values. If none of the three consecutive sample values are equivalent, the voting scheme determines which of the three values was the first sampled value and that value is declared to be the valid data value (120). The reason for this is that if the second and third values are not equivalent, then the data transition is expected to have occurred sometime after the first sample was obtained based on the parameters established for obtaining the samples.

The criteria for selecting the valid data value from a set of three consecutive samples can be expressed in the form of the following expression: if data 3 is equal to data 2 then pick data 3; else pick data 1. With the benefit of this disclosure, one skilled in the art can obtain alternative expressions for implementations utilizing three samples or even sample numbers other than three including numbers greater than three samples. The predetermined criteria may be stored in a memory segment of the receiving circuit, the transmitting circuit, or other memory location in a component of IMD 20, such as the data transfer module, or other memory including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In the exemplary embodiment where the data transfer module resides in the second (transmitting) circuit, the valid data value (as determined at 118 or 120) is then transmitted to the first (receiving) circuit (122). In general, the data will be transmitted from the second (transmitting) circuit to the first (receiving) circuit through a communication channel such as a data bus or a data connection line with the connection linking the two circuits being direct or through a coupling component. In one embodiment, the communication channel or coupling medium is the standard serial peripheral interface (SPI) bus.

For purposes of illustrating operation of the voting scheme and without intending to be limiting, an exemplary data transfer operation for IMD 20 is discussed. Assume, in the example that a read request has been issued by a first component, such as the microprocessor 30 that is operating at the higher frequency speed, e.g., 700 KHz, for data that is communicated through the SPI bus and obtained from a second component, such as the DSP 36 that is operating at a lower frequency speed e.g., 5 KHz.

FIGS. 6A-6F each depict an illustrative case scenario during a read operation by the first component utilizing the voting scheme. The depicted scenarios are believed to be useful in aiding in the understanding of the voting scheme. As such, the scenarios are not exhaustive of all possible scenarios nor are they intended to be limiting of the aspects of this disclosure. For context, the figures depict a set of scenarios under which three samples are obtained. However, the specific number of samples obtained will vary depending on the implementation of the voting scheme and it should therefore be understood that reference to a particular number, such as the three (3) samples as illustrated in examples in this document, is not intended to be limiting. Rather, the reference to three samples is merely intended to aid in a meaningful description of the aspects of the invention.

In the figures, a data signal 82 denotes the data that is to be communicated from the second component to the first component. As those skilled in the art will appreciate, the values of the data signal 82 will transition at the active clock edges of the clock signal that clocks the transmitting component; in this case, the second (slower) clock signal (not shown). A first (faster) clock signal 84 represents the clock signal that clocks the first component. The arrows in the first clock signal 84 denote the active edges within which the first component performs a sampling of the data transmitted from the second component. In this example, the first component samples data at both the rising and falling edges of the first clock signal. Superimposed within the data signal 82 are the values of the data transmitted from the second component to the first component. In this exemplary implementation, denoted in hexidecimal format, the data value is a "7" prior to the first transition, and this value transitions to an "8" as illustrated. During the transition window, TW, the data is indeterminate; that is, the value could be a "7" or an "8" or an "F." It is expected that the data value will switch between the three possible values during the transition interval which, again, occurs on or around the active clock edges of the second (slower) clock signal. Therefore, sampling the data at any point in time within the transition window, TW, would yield any one of the three values.

Figure 6A:
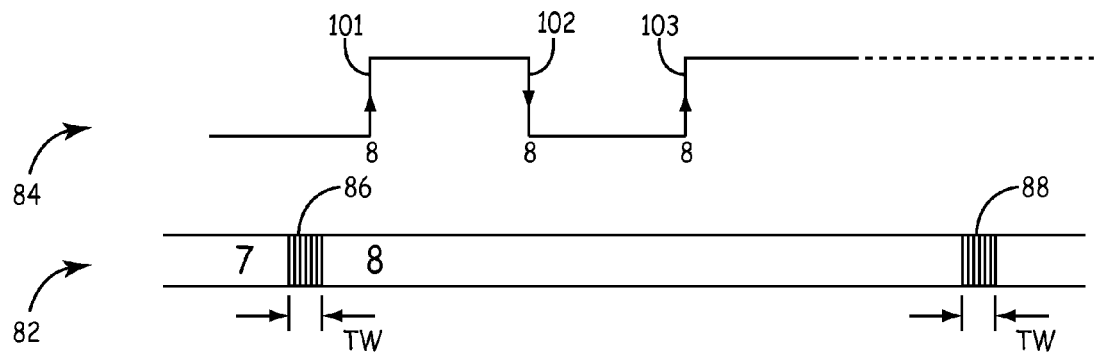
FIGS. 6A-6F depict illustrative case scenarios during a read operation in accordance with an embodiment of the disclosure.

Turning to FIG. 6A, the scenario depicted in the illustration shows a first transition window 86 that occurs prior to a first sampling 101 of data signal 82 and a second transition window 88 that occurs after a third sampling 103 of the data signal 82. Therefore, at the time of first, second, and third sampling, the data value has already transitioned from a 7 to an 8. The first sampling 101, second sampling 102, and third sampling 103 correspond to the active edges of the first clock signal 84—in this example, both rising and falling edges are active. As depicted, the resulting sampled values are all the same, i.e., the first sampling 101 of the data signal 82 yields a value 8, as does the second sampling 102 and the third sampling 103. Each of the first, second and third sample values are compared to each other. Because the comparison yields the same value, the valid data value is deemed to correspond to the last sampled value. In this case that valid value is reported as 8.

Figure 6B:
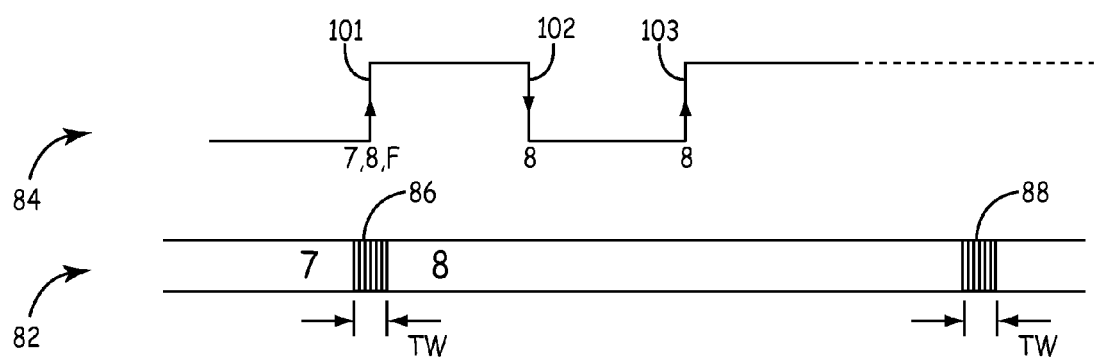

FIG. 6B illustrates a scenario under which the transition window 86 occurs concurrently with the first sampling 101 which is at the first rising edge of clock signal 101. The transition window 88 will occur at a point in time after the third sampling 103. The data sampled at the first sampling 101 may be one of three values, i.e., 7, 8, or F because of the data transition corresponding to the first sampling 101 point. Because the transition window 86 ends prior to the second sampling 102 point, the data value sampled at the second sampling 102 is stable. That value is 8 in this example. As for the third sampling 103, the data will still be stable and because the second transition window 88 does not occur until after the third sampling 103, the data value sampled again is 8. The first, second, and third sampled values are then compared to derive the valid data value. According to the voting scheme, if the second and third values are identical but differ from the first value, then the valid data value is deemed to be the third value. In this case, the valid data value is reported as 8.

Figure 6C:
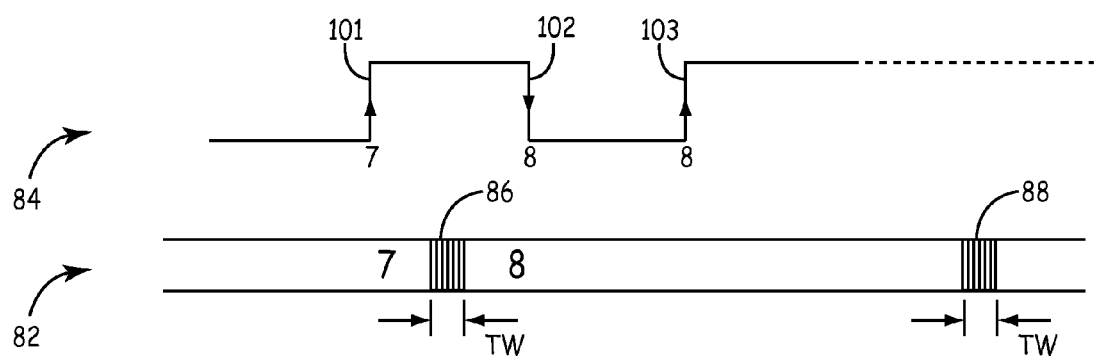

FIG. 6C depicts a third scenario under which the transition window 86 occurs between the first sampling 101 and the second sampling 102. The transition window 88 will occur at a point in time after the third sampling 103. Because the transition of the data occurs subsequent to the first sampling 101 and before the second sampling 102, the data value sampled at 102 will differ from the first sample 101. However, the data value sampled at the second sampling 102 is the same value sampled at the third sampling 103. Therefore, this scenario yields three sample values that are similar to those obtained in the FIG. 6B example and the analysis under the voting scheme results in a similar determination of the valid data value (8).

Figure 6D:
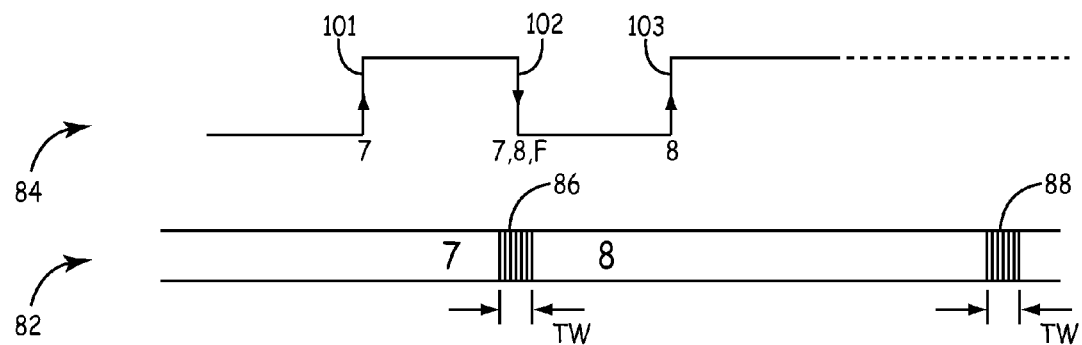

FIG. 6D shows a scenario in which the transition window 86 occurs concurrently with or within the second sampling 102, which is performed at a falling edge. The transition window 88 will occur at a point in time after the third sampling 103. Unlike the scenario in FIG. 6C, the second sampling 102 may result in a reading of an indeterminate value. That is because the second sampling is performed at some time during the transition window 86 when the data value may be 7, 8 or F. Assuming as was the case with FIG. 6B that this indeterminate value corresponds to neither the value prior or the value after the transition, all three sampled values will be different. For completeness, the first sampling will result in a reading of the data value 7 and the third sampling will result in a reading of the data value 8 following the transition at transition window 86. Here, because the second and third data values are not identical, the voting scheme deems the data value sampled at first sampling 101 (7) to be the valid data value.

Figure 6E:
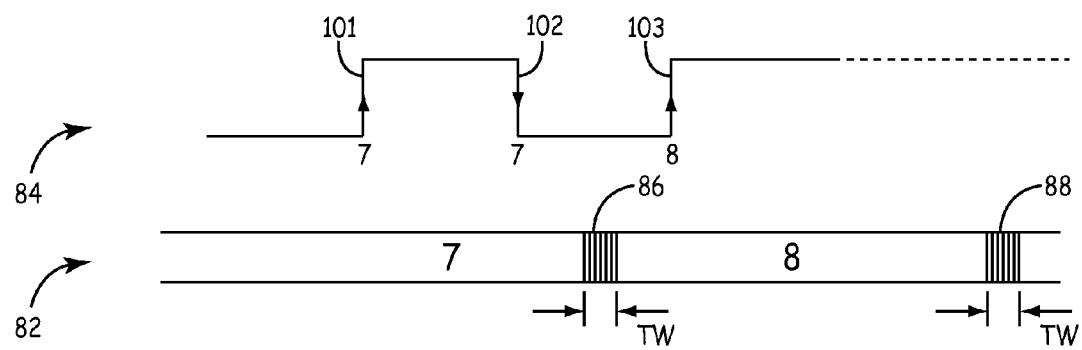

FIG. 6E depicts the scenario under which the transition window 86 occurs between the second sampling 102 and the third sampling 103. The transition window 88 will occur at a point in time after the third sampling 103. Because the transition window 86 occurs after the second sampling 102 and before the third sampling 103, the data value obtained at the first sampling 101 will correspond to the data obtained at the second sampling 102. In this example, that data value is (7). The third sampling 103 will yield the data value (8) because the transition has already occurred after transition window 86. In this scenario, the comparison is performed for the sample values obtained at the first sampling 101, the second sampling 102, and the third sampling 103. The result of this comparison is that the values obtained at the second sampling and third sampling are not identical. Therefore, the voting scheme reports the value obtained at the first sampling (7) as the valid data value.

Figure 6F:
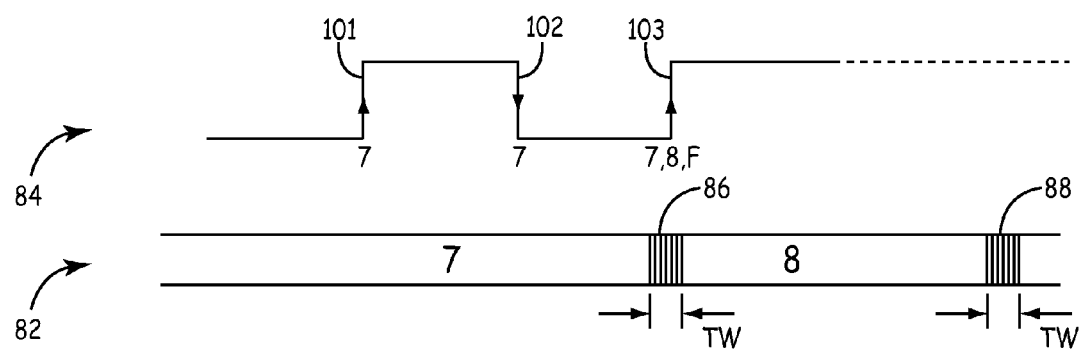

FIG. 6F shows a scenario in which the transition window 86 occurs concurrently with or around the third sampling 103, which is performed at a rising edge. The transition window 88 will occur at a point in time after the third sampling 103. In this example, the first sampled value and the second sampled value are both identical, i.e., 7, while the third sampled value 8 differs. Pursuant to the voting scheme, the valid data value is reported as 7 because the first and second sampled values are equivalent.

For ease of illustration, the case scenarios depict an implementation that utilizes three samples. However, the samples can be any number in excess of two. Those skilled in the art can appreciate that the specific number of samples is a design choice that is nonetheless within the scope of this disclosure. Moreover, it should be noted that these scenarios contemplate sampling by the data transfer module with a timing relationship such that the first transition window 86 will occur in the period between sometime before the first sampling 101 up to or concurrently with the third sampling 103. Nevertheless, other timing relationships can be extrapolated from this implementation wherein the number of samples to be obtained can be varied and/or the relationship between the speeds of the first clock signal and the second clock signal may differ. Such considerations are merely a matter of routine implementation and the inventor believes that this disclosure need not be unduly obscured in an effort to describe such mundane details.

The above detailed description includes references to the accompanying drawings, which form a part of the detailed description. The drawings show, by way of illustration, specific embodiments in which the disclosure can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the terms "including" and "in which" are used as the plain-English equivalents of the respective terms "comprising" and "wherein." Also, in the document, the terms "including" and "comprising" are open-ended, that is, a system, device, article, or process that includes elements in addition to those listed after such a term in a claim are still deemed to fall within the scope of that claim. Moreover, in the document, the terms "first," "second," and "third," etc. are used merely as labels, and are not intended to impose numerical requirements on their objects, unless otherwise denoted. The terms "circuit" or "circuitry" or "component" or "module" or "chip" should be understood as being interchangeable wherever they appear in this document. In addition, the various aspects of the circuit, circuitry, component, module or chip may not necessarily reside in a single or unitary unit but rather may be implemented in multiple units while still achieving the functions described herein.

Aspects of implementation of the voting scheme within a data transfer module as described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), non-volatile random access memory (NVRAM), electrically erasable programmable read-only memory (EEPROM), FLASH memory, magnetic data storage media, optical data storage media, or the like.

The term "processor" or "processing circuitry" may generally refer to any of the foregoing logic circuitry, alone or in combination with other logic circuitry, or any other equivalent circuitry. Further, the present disclosure is not limited in scope to implantable medical devices but extends to devices of all types including low power devices.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. It should also be understood that various changes can be made in the function and arrangement of elements without departing from the scope of the disclosure as set forth in the appended claims and the legal equivalents thereof.

What is claimed is:

1. A circuit for transferring data between a first circuit clocked by a first clock signal having a first frequency and a second circuit clocked by a second clock signal having a second frequency, comprising:

means for establishing a sampling window for a plurality of samples of data communicated from the second circuit to the first circuit, wherein the sampling window has a duration that is less than a single clock cycle of the second clock signal;

means for establishing a sampling period between each of the plurality of samples, wherein the sampling period is greater than a transition window and less than the sampling window;

means for obtaining the plurality of samples of the data from the second circuit, wherein the plurality of samples are obtained within the sampling window and each of the plurality of samples is obtained a sample period apart;

means for comparing each of the plurality of data samples; and means for declaring the valid data value based on the comparison.

2. The circuit of claim 1, wherein the sampling window is less than the interval between two successive transitions of the data minus the transition window of the second circuit.

3. The circuit of claim 2, wherein the transition window corresponds to the window of time during which the data is unstable following an active clock edge of the second circuit.

4. The circuit of claim 1, wherein the sampling window corresponds to one clock cycle of the second clock signal minus the transition window of the second circuit.

5. The circuit of claim 1, wherein the clock cycle is defined to be the interval between two consecutive clock edges of the same polarity.

6. The circuit of claim 1, wherein the sampling period of each of the plurality of samples is based on a duration of the transition window of a data value of the data signal at the second circuit.

7. The circuit of claim 6, wherein the sampling period is greater than the transition window of the data value.

8. The circuit of claim 1, wherein the number of plurality of obtained data samples is three.

9. The circuit of claim 1, wherein the declaring means declares the valid data value of the data signal to be either the third data sample in response to the third data sample being equivalent to the second data sample or the first data sample in response to the third data sample not being equivalent to the second data sample.

10. The circuit of claim 1, wherein the comparing means performs a comparative analysis comprising evaluating each of the plurality of data samples based on predetermined criteria to determine a valid data value of the data signal.

11. An implantable medical device having a first circuit clocked by a first clock signal having a first frequency in communication with a second circuit clocked by a second clock signal having a second frequency that is different from the first frequency, comprising:

means for determining a sampling window for a plurality of samples of data communicated from the second circuit to the first circuit, wherein the sampling window has a duration that is less than a single clock cycle of the second clock signal;

means for defining a transition window of the data in the second circuit following an active edge of the second clock signal, wherein the transition window corresponds to a duration of time during which the data is unstable following an active clock edge of the second circuit;

means for determining a sampling period between each of the plurality of samples, wherein the sampling period is greater than the transition window;

means for obtaining the plurality of samples of the data from the second circuit, wherein the plurality of samples are obtained within the sampling window and each of the plurality of samples is obtained a sample period apart;

means for comparing each of the plurality of data samples; and means for declaring the valid data value based on the comparison.

12. The device of claim 11, wherein the sampling window is a duration that corresponds to an interval between two consecutive active edges of the second clock signal minus the transition window of the data within the second circuit.

13. The device of claim 12, wherein the sampling window corresponds to one clock cycle of the second clock signal minus the transition window of the data.

14. The device of claim 11, wherein the sampling period is greater than the transition window and less than the sampling window.

15. The device of claim 11, wherein the sampling period of each of the plurality of samples is based on a duration of the transition window of a data value of the data signal at the second circuit.

16. The device of claim 11, wherein the declaring means declares the valid data value of the data signal to be either the third data sample in response to the third data sample being equivalent to the second data sample or the first data sample in response to the third data sample not being equivalent to the second data sample.

17. The device of claim 11, wherein the comparing means performs a comparative analysis comprising evaluating each of the plurality of data samples based on predetermined criteria to determine the valid data value of the data signal.

18. The device of claim 11, wherein an interval between each one of the obtained plurality of samples within each given sampling window is greater than the transition window.

* * * * *